United States Patent
Niederberger

[11] Patent Number: 5,810,772
[45] Date of Patent: Sep. 22, 1998

[54] MOTHER'S MILK PUMP

[75] Inventor: Anton Niederberger, Oberdorf, Switzerland

[73] Assignee: Trimed AG, Triesen, Liechtenstein

[21] Appl. No.: 654,199

[22] Filed: May 28, 1996

[30] Foreign Application Priority Data

May 26, 1995 [CH] Switzerland ............ 01557/95

[51] Int. Cl.⁶ .......................................... A61M 1/06
[52] U.S. Cl. ........................................ 604/74; 604/346
[58] Field of Search ..................... 604/73, 74, 131; 417/413.1

[56] References Cited

U.S. PATENT DOCUMENTS

| | | |
|---|---|---|
| 3,238,937 | 3/1966 | Stein . |
| 4,607,596 | 8/1986 | Whittlestone et al. . |
| 4,857,051 | 8/1989 | Larsson . |
| 4,929,229 | 5/1990 | Larsson . |
| 4,964,851 | 10/1990 | Larsson . |
| 5,007,899 | 4/1991 | Larsson ........................ 604/74 |
| 5,304,129 | 4/1994 | Forgach . |
| 5,492,449 | 2/1996 | Hunklinger et al. ............ 417/259 |
| 5,514,166 | 5/1996 | Silver et al. ................... 604/74 |
| 5,542,921 | 8/1996 | Meyers et al. ................. 604/74 |
| 5,571,084 | 11/1996 | Palmer ........................ 604/74 |
| 5,601,531 | 2/1997 | Silver ........................ 604/74 |
| 5,616,125 | 4/1997 | Jelks ......................... 604/74 |

FOREIGN PATENT DOCUMENTS 9625187  8/1996  WIPO .

Primary Examiner—Wynn Wood Coggins
Assistant Examiner—Deborah Blyveis
Attorney, Agent, or Firm—Martin A. Farber

[57] ABSTRACT

In a pump for pumping mother's milk, at least one funnel-like breast body is connected to a vacuum conduit in order to pump mother's milk into a milk collection container. To this end, the pump comprises at least one suction chamber and a conduit system leading out from said suction chamber. The conduit system is to be connected with the vacuum conduit and the funnel-like breast body. While a pumping unit applies vacuum to the suction chamber, an interrupting device interrupts the vacuum applied to the suction chamber cyclically during a predetermined cycle period. There is a control device for controlling the cycle period.

3 Claims, 1 Drawing Sheet

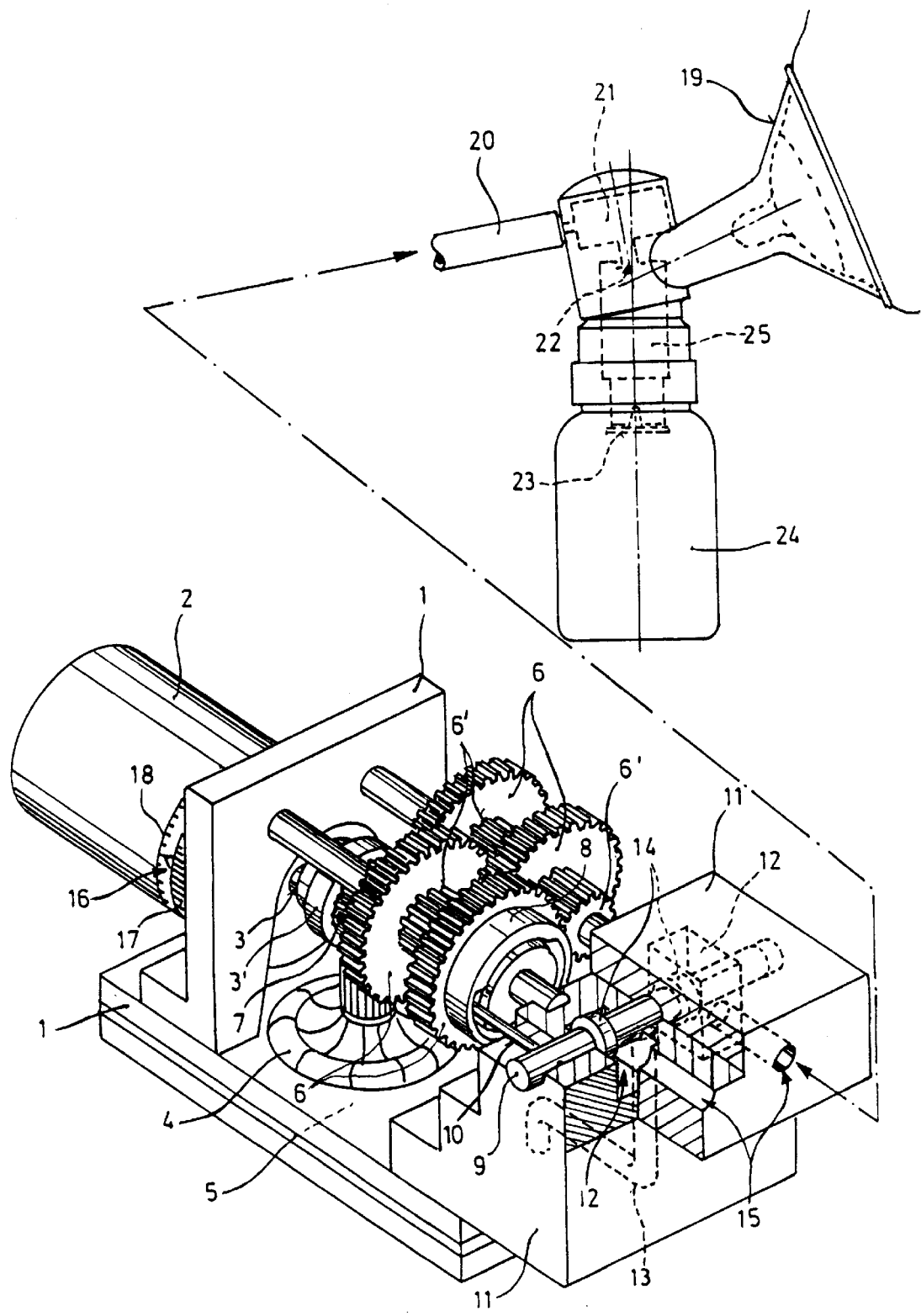

MOTHER'S MILK PUMP

FIELD OF THE INVENTION

The present invention relates to a pump for pumping mother's milk by connecting it with at least one funnel-like breast body over a vacuum conduit in order to pump mother's milk into a milk collection container.

BACKGROUND OF THE INVENTION

Known mother's milk pumps are for sucking and collecting mother's milk so that a baby can also be nourished even if his mother is not present. They are used, however, if the baby has difficulties in sucking on the mother's breast or if the mother produces too large or too small an amount of mother's milk.

In U.S. Pat. Nos. 4,929,229 and 4,857,051, a mother's milk pump is disclosed comprising a funnel-like breast body to be applied to the breast, the breast body being connected to a manually actuable plunger pump by means of a vacuum conduit wherein a milk collection container is arranged. Vacuum is generated by the plunger pump during its suction stroke.

Although this mother's milk pump worked in general satisfactorily, it exhibits some drawbacks. For example, this mother's milk pump is expensive, relatively difficult and cumbersome to use, and cannot suck from two breatss simultaneously, thus wasting time.

SUMMARY OF THE INVENTION

It is an object of the present invention to provide a mother's milk pump at a lower price, which is light in weight and is simple to operate.

Another object is to enable sucking simultaneously from two breasts, if so desired.

It is a further object of this invention to provide a mother's milk pump where milk can be sucked off in a natural suction rhythm, thus avoiding injuries and inflammations of the mother's breast, mostly resulting from sucking too intensely.

According to the invention two Connections are provided for enabling connection to a respective breast body.

Furthermore, it is preferred to interrupt cyclically the vacuum applied in a controlled manner during a predetermined cycle period.

It is especially favorable, if a pair of conduits are provided, which is each adapted to be connected to one funnel-like breast body, so that vacuum can be applied alternately to one and the other of said pair of conduit means. In this manner, in contrast to the prior art where the pump could only be successively used on an individual one of mother's breasts, time necessary for sucking mother's milk off is reduced. Moreover, by alternately interrupting the vacuum applied, the pump has not to provide the whole power for sucking milk from both breasts simultaneously so that its power is distributed over time. In this way, a smaller and less expensive pump can be used.

In order to adapt the suction cycle to the natural suction cycle of a baby, the control means are designed to cyclically interrupt the vacuum applied with a frequency of 60 suction cycles per minute in maximum, preferably to interrupt it 30 to 50 times per minute, for example 40 times. In doing this, it is preferred if the time of interruption is equal to the time of suction.

An individual adaptation of the suction cycle time can be achieved by providing an adjusting device for adjusting the duration of said cycle period.

BRIEF DESCRIPTION OF THE DRAWING

An embodiment of a mother's milk pump according to the invention will be described below with reference to the only FIGURE of the drawing which shows schematically a perspective view of a mother's milk pump omitting a housing lid which completes the outlines shown to about a parallelepiped.

DETAILED DESCRIPTION OF THE DRAWING

An electric motor 2 is connected to a component support 1 of a mother's milk pump and drives a drive shaft 3, the end of which being formed with an eccentric drive 3' for driving a membrane pump 4 of known design. The membrane pump 4 is to evacuate a vacuum space 5 within the bottom part of the support 1. It will be understood that also a plunger pump or any other pump, such as a peristaltic pump, could be used instead of a membrane pump 4, but tests have shown that a membrane pump is optimal for the intended purpose.

Within the component support 1, gear wheels 6, 6' of a reduction gear are journaled by two shafts parallel to each other, the reduction gear being driven by a gear wheel 7 mounted on the drive shaft 3. The reduction gear can be of any type, especially being variable, and could be formed, for example, at least in part by a belt drive, e.g. a V-belt drive, in order to enable an adjustment of cycle time by means of an appropriate adjusting mechanism, for example being of the PIV-type. Another method for adjusting the cycle time and the number of revolutions may consist in the arrangement of a potentiometer 16 within the circuit of the motor 2. This potentiometer 16 can be adjusted by means of a knob 17 along a dial 18 for adjusting the number of revolutions of the motor 2, thus adapting the suction effect and the cycle time as desired.

A further adjustment facility could include an adjustable throttle valve in connection with the vacuum space 5. Such throttle valve could either communicate the vacuum space 5 with the environment, thus acting as a kind of a pressure relief valve for maintaining a predetermined pressure within the vacuum space 5. Preferably, however, it is inserted in the conduit system 12, 13, 15, thus allowing only a restricted pressure to reach the outlets 15 in a controlled manner.

At the output end of the reduction gear 6, 6', a control device 8–10 is provided. In a manually driven breast pump, the control device 8–10 could simply consist of a throttle valve imposing a certain rhythm to the pumping motion. Preferably, however, the pump and/or the control device 8–10 are driven by an electric motor which better ensures uniform suction.

In this case, the control device 8–10 preferably comprises a cam-like control disk 8 having a control groove which is engaged by a cam follower pin 10 connected to a control rod 9. This control rod 9 forms the actuation part of a valve member and is alternately moved to and fro by the control disk 8 in a direction perpendicular to the longitudinal direction of the control pin 10. Alternatively the control mechanism 8–10 is adapted to impart a rotary motion to a control shaft 9 for opening or closing a valve to be described below.

A portion of the component support 1 is formed as a control block 11 including two identical suction chambers 12 for housing a valve to be described below. The suction chambers 12 are part of a conduit system which is opened and closed by the translatory movement of the control rod 9, in open condition being connected to the vacuum space 5 through a connecting conduit 13 opening in the middle between the two chambers 12, or each through a respective connecting conduit 13. It would be possibly to accommodate the valve member 9 directly within the vacuum space 5 which, then, functions as a suction chamber, thus, avoiding separate ones.

It will be recognized that the combination of a vacuum space, which "integrates" the pumping pulses of the membrane pump, and the suction chambers 12 enables a uniform distribution of the suction pressure to both suction chambers 12 and their outlets. A further contribution is made by the common valve member 9, because in the case of employing two independent valves, synchronizing problems could arise.

In order to seal the vacuum chambers 12 from each other or from the conduit system 13, 15 under all operational conditions, the control rod 9 comprises two sealing members or control flanges 14 appropriately spaced from each other. The conduit system comprises an outlet bore 15 assigned each to a respective suction chamber with which the respective end of a suction hose 20 communicates, the other end being connected to a funnel-like breast body 19. Alternatively, the two control flanges cooperate each with the respective outlet bore 15. The end of the suction hose 20 connected to the breast body 19 opens into a vacuum chamber 21, communicating with a suction space 25 which is unidirectionally closed against a milk collection container 24 by means of a check valve 23.

Although only one breast body 19 is shown, it has to be understood that in accordance with a preferred embodiment of the invention each of the two outlet bores 15 is connected to one breast body 19 supplying either into a separate milk collection container 24 each or into a common milk collection container. In the latter case, both breast bodies can optionally be interconnected, if desired, in an adjustable distance from each other, e.g. formed in the manner of a bra. It would also be conceivable to provide a single suction chamber 12 with two outlet bores 15 being alternately connected to the vacuum source (or space 5) by the control device 8–10.

It will be understood that it is within the scope of the invention to form the control device in any way desired, particularly as an electronic control device in which, for example, the output signal of an astable time-base circuit, after amplification, is applied to a valve manner corresponding in function to the control rod 9. Theoretically, it would also be possible to render the number of revolutions of the electric motor 2 adjustable, as has been described above with reference to rotational potentiometer 16. In the case of a single breast body 19, the control device could even simply comprise a switch within the motor's circuit for switching it cyclically on and off, thus, obtaining a suction frequency of 60 times per minute in maximum. However, the control device 8, 9, as shown, is characterized by a particular sturdiness.

For security reasons, the electric motor 2 is preferably supplied with 12 volts in maximum, e.g. with a battery current of only 3 volts, and can suitably be connected to the network system through a transformer, but a battery as a current source, as mentioned, could also be used. Preferably, the electric motor rotates with 3000 to 6000 r.p.m., e.g. with 5000 r.p.m., so that the membrane of the membrane pump 4 is lifted and lowered by means of the excentric 3' at a corresponding frequency. The gear wheels 6, 6' of the reduction gear are chosen in such a manner that the control disk 8 displaces the control rod 9 to and fro by means of the cam follower 10 in a desired suction rhythm of 60 times per minute in maximum, for example 40 times per minute. In this manner, the control disk 8 controls the cycle period of the control rod 9 which opens one of the suction chambers 12 during this period, while closing the other. Preferably, the control disk 8 is formed in such a manner that the cycle time determined by the control device 8, 9 is equal for both breast bodies (i.e. the respective duration of opening and closing one of the suction chambers is equally long), although a mode of operation with unequal cycle periods may also be suitable in some cases. For the latter mode of operation, the control disk 8 could, for example, be releasably connected to the adjacent gear wheel 6, for example in a positive manner, such as by plugged pins, and could be replaceable in this way in order to be able to adjust the cycle period or the ratio of opening and closing durations.

In this manner, each suction chamber 12 is connected to the vacuum space 5 60 times per minute in maximum, e.g. 40 times, so that each breast body 19 applied to the mother's breast sucks milk off by an applied vacuum at a frequency of 60 times per minute in maximum, e.g. 40 times, the milk being collected within the milk collection container 24 which is connected to the breast body 19 or the suction hose 20, as known per se. In order to obtain a particularly light weight mother's milk pump, as many parts of it as possible are made from plastic material.

In case only one mother's breast has to be sucked for any reason, this can easily be done by applying only one breast body 19 to the mother's breast. Likewise, it is within the scope of the invention to construct the pump for connection with a single breast body 19 connected to a single suction chamber 12 (where the pump optionally comprises only a single suction chamber 12), whereas the other suction chamber 12 sucks only by-padded air or is connected to a bellow.

What is claimed is:

1. A pump for pumping mother's milk by connecting it with a pair of funnel-like breast bodies via a corresponding pair of vacuum conduits in order to pump mother's milk into a milk collection container, the pump comprising:

suction chamber means providing a vacuum;

a conduit system leading out from said suction chamber means to be connected with said pair of vacuum conduits for communication of said vacuum to said pair of funnel-like breast bodies;

pumping means connecting with said suction chamber means for applying said vacuum to said suction chamber means;

an electric motor means; and wherein said pumping means comprises a membrane pump driven by said electric motor means;

said membrane pump comprises:

a vacuum generation space;

pumping membrane means at least partially delimiting said vacuum generation space;

eccentric means operatively connected to said pumping membrane means for moving said pumping membrane means to and fro relative to said vacuum generation space; and wherein said pump further comprises control means, operatively connected to said pumping membrane means for alternately connecting with each vacuum conduit the vacuum generated within said vacuum generation space.

2. Pump as claimed in claim 1, wherein said suction chamber means comprises a pair of suction chambers connected with said pair of vacuum conduits.

3. A pump for pumping mother's milk by connecting it with a pair of funnel-like breast bodies via a corresponding pair of vacuum conduits in order to pump mother's milk into a milk collection container, the pump comprising:

suction chamber means providing a vacuum;

a conduit system leading out from said suction chamber means to be connected with said pair of vacuum conduits for communication of said vacuum to said pair of funnel-like breast bodies;

pumping means operatively connected with said suction chamber means for applying said vacuum to said suction chamber means;

interrupting means for determining a cycle of interruption of said vacuum applied to said suction chamber means by said pumping means during a predetermined cycle period; and control means operatively connected to said pumping means for controlling said cycle period;

wherein said interrupting means comprises valve means between said pumping means and said conduit system, and means for actuating said valve means;

said control means comprises drive means including a drive shaft, and cam means on said drive shaft for controlling said cycle period; and said cam means is connected with said actuating means for said valve means.

* * * * *